United States Patent
Haase et al.

(10) Patent No.: US 7,798,789 B2
(45) Date of Patent: Sep. 21, 2010

(54) REDUCING CYLINDER WEAR IN A DRUG PUMP

(75) Inventors: James M. Haase, Maplewood, MN (US); Ronald L. Mezera, Lake Elmo, MN (US); Nicholas R. Whitehead, Hopkins, MN (US)

(73) Assignee: Medtronic, Inc., Minneapolis, MN (US)

( * ) Notice: Subject to any disclaimer, the term of this patent is extended or adjusted under 35 U.S.C. 154(b) by 271 days.

(21) Appl. No.: 11/749,460

(22) Filed: May 16, 2007

(65) Prior Publication Data

US 2008/0286132 A1     Nov. 20, 2008

(51) Int. Cl.
F04B 35/04 (2006.01)
F01B 31/00 (2006.01)
H02K 7/06 (2006.01)

(52) U.S. Cl. .................... 417/417; 92/173; 310/20
(58) Field of Classification Search ............. 417/413.1, 417/410.1, 417, 44.1, 415, 416; 92/173; 310/14, 15, 20, 23, 37
See application file for complete search history.

(56) References Cited

U.S. PATENT DOCUMENTS

| | | | | |
|---|---|---|---|---|
| 2,944,520 A * | 7/1960 | Swanson | ...................... | 60/716 |
| 2,995,122 A * | 8/1961 | Randall | ...................... | 123/46 R |
| 4,125,978 A * | 11/1978 | Schildge, Jr. | ............... | 52/223.1 |
| 4,412,418 A * | 11/1983 | Beale | .................... | 60/520 |
| 4,493,314 A * | 1/1985 | Edwards, II | .................... | 600/16 |
| 4,573,994 A | 3/1986 | Fischell et al. | | |
| 4,697,622 A | 10/1987 | Swift et al. | | |
| 4,919,104 A * | 4/1990 | Hensel et al. | ............... | 123/533 |
| 5,167,633 A | 12/1992 | Mann et al. | | |
| 5,176,644 A | 1/1993 | Srisathapat et al. | | |
| 5,514,103 A | 5/1996 | Srisathapat et al. | | |
| 5,660,534 A * | 8/1997 | Snow | ......................... | 417/554 |
| 5,818,131 A * | 10/1998 | Zhang | ......................... | 310/15 |
| 5,893,708 A * | 4/1999 | Nelson, II | .................... | 417/456 |
| 6,530,363 B1 * | 3/2003 | Blass et al. | .................. | 123/446 |
| 6,595,756 B2 * | 7/2003 | Gray et al. | .................. | 417/44.1 |
| 6,652,510 B2 | 11/2003 | Lord et al. | | |
| 6,932,584 B2 * | 8/2005 | Gray et al. | .................. | 417/417 |
| 7,131,967 B2 * | 11/2006 | Gray et al. | ............... | 604/891.1 |
| 7,419,367 B2 * | 9/2008 | Rijnberg | .................... | 417/416 |
| 2004/0126253 A1 * | 7/2004 | Gray et al. | .................. | 417/417 |

(Continued)

FOREIGN PATENT DOCUMENTS

DE     4243866     6/2004

(Continued)

OTHER PUBLICATIONS

International Search Report from PCT/US08/061094 mailed Aug. 29, 2008.

*Primary Examiner*—Charles G Freay
(74) *Attorney, Agent, or Firm*—Scott A. Marks, Esq.

(57) ABSTRACT

The present invention relates to a method and related apparatus for rotating a piston of a drug pump during the pumping stroke to reduce drug pump wear. The actuator may move a piston that pumps fluid through a pumping channel. In the present invention, the armature includes one or more openings or shapes that cause the actuator, including the armature and the piston, to rotate about a longitudinal axis of the piston during the pumping stroke. Rotation of the actuator member may help to reduce wear to the actuator member and the pump itself caused by repetitive pumping motions.

20 Claims, 7 Drawing Sheets

U.S. PATENT DOCUMENTS

| | | | |
|---|---|---|---|
| 2004/0219041 A1* | 11/2004 | Rijnberg | 417/416 |
| 2005/0024175 A1* | 2/2005 | Gray et al. | 335/220 |
| 2005/0075624 A1 | 4/2005 | Miesel et al. | |
| 2006/0056998 A1* | 3/2006 | Gray et al. | 417/413.1 |
| 2006/0207922 A1* | 9/2006 | Dussich | 210/164 |
| 2007/0086904 A1* | 4/2007 | Gray | 417/417 |

FOREIGN PATENT DOCUMENTS

| | | |
|---|---|---|
| EP | 0760244 | 3/1997 |
| EP | 1878920 | 1/2008 |
| WO | 02083208 | 10/2002 |
| WO | 03023226 | 3/2003 |

\* cited by examiner

REDUCING CYLINDER WEAR IN A DRUG PUMP

FIELD

This invention relates generally to a drug pump. More particularly, the present invention relates to a method and related apparatus for rotating a piston of a drug pump during the pumping stroke to reduce drug pump wear.

BACKGROUND

Infusion devices may be used to deliver an infusion media (e.g. a medication such as insulin) to a patient. Such devices may be designed to be implanted into a patient's body to deliver predetermined dosages of the infusion media to a particular location within the patient's body, e.g. in the venous system, the spinal column, or within the peritoneal cavity. A known infusion device of the type described above includes a drive mechanism that includes a reciprocating pumping element, otherwise known as an actuator member. The reciprocating pumping element includes an actuator that has a piston portion coupled to an armature portion, also known as a piston actuator or pole. The piston portion is configured to reciprocate within a piston channel when a solenoid coil is alternately energized and de-energized. That is, when the solenoid is energized, magnetic flux causes the actuator to move very quickly (i.e. in the order of 2-3 milliseconds) until it reaches a stop member. This corresponds to the pump's forward stroke and results in the delivery of a predetermined dosage of infusion media from an outlet chamber to the patient. When the solenoid is de-energized, the lack of magnetic flux allows the actuator to return to its original position under the force of a spring or other return mechanism. This, in turn, causes the pressure in the piston chamber to fall. The reduced pressure in the piston chamber causes infusion media to flow from a reservoir through an annulus between the actuator piston and the piston cylinder wall to refill the piston chamber, thus equalizing the pressure between the reservoir and the piston chamber and preparing the pump for its next pumping or delivery stroke. This is referred to as the refill stroke. The annulus between the actuator piston and the piston cylinder may be very small (i.e. in the order of 150 to 250 microinches radially), resulting in an outlet chamber refill process that takes between about 1 to 2 seconds. In contrast, the pump's forward (delivery) stroke may be approximately 500 times faster than the refill process.

Over time, the motion of the piston back and forth may result in wear. Furthermore, uneven loads may have a tendency to tip the piston to one side of the cylinder or the other. Tipping of the piston may continuously wear a single location on the piston or cylinder, resulting in not-insignificant long term damage. Modifications to the piston, cylinder, and other corresponding pieces of a drug pump that reduce this wear are therefore continuously desired.

BRIEF SUMMARY OF THE INVENTION

According to an aspect of the invention, a method of causing rotation of a pump piston/actuator in a cylinder of a piston type drug infusion pump is disclosed. In one embodiment, the rotation of the piston may be achieved by the formation of passages in the piston actuator. The movement of fluid through passages of a certain size and shape during the pumping process may induce the rotation of the piston in the piston cylinder some predetermined amount at every stroke. The movement of the piston in the cylinder, the wear caused by the movement of the piston will be more distributed around the periphery, leading to less degradation of the piston and other components over time.

One embodiment may be an actuator member for a fluid pumping device that includes an armature portion, a piston portion operably connected to the armature portion, and one or more openings formed through the armature portion at an angle whereby when a fluid flows through the openings the actuator member rotates about an axis represented by the piston.

Another embodiment may be an actuator for delivering fluid through a piston channel from an inlet to an outlet, the actuator including an armature configured to move between a first position and a second position, the armature including one or more contours formed in the armature, and a piston coupled to the armature and moveable within the piston channel, whereby movement of the armature and piston from the first position to the second position causes the actuator to rotate around a longitudinal axis of the piston.

Yet another embodiment may include an apparatus for delivering a fluid, the apparatus comprising a housing, an inlet in the housing for receiving the fluid, an outlet in the housing for discharging the fluid, a piston channel within the housing through which the fluid flows from the inlet to the outlet, and an actuator positioned within the housing and moveable between a first position and a position, the actuator defining a piston chamber for storing fluid received through the inlet when the actuator is in the retracted position, the actuator driving the fluid stored in the piston chamber toward the outlet when the actuator transitions from the retracted position to the forward position, the actuator further including an armature including one or more openings therethrough, and a piston coupled to the armature and moveable within the piston channel, whereby when the fluid flows through the openings of the armature the actuator is caused to rotate around an axis.

BRIEF DESCRIPTION OF THE DRAWINGS

Embodiments of the present invention will hereinafter be described in conjunction with the following drawings wherein like reference numerals denote like elements throughout.

DETAILED DESCRIPTION OF THE INVENTION

The present invention is an actuator member of a piston pump that includes shapes or openings through an armature portion to cause the actuator member to rotate around an axis represented by a piston during the pumping stroke. Rotation of the actuator member may help to reduce wear to the actuator member and the pump itself caused by repetitive pumping motions. In some cases, the actuator may have a small manufacturing defect on one portion of the actuator that causes wear, but the defect is moved so as to wear at different locations on the pump rather than on the same location in a repetitive manner.

The following detailed description is of the presently contemplated mode of implementing the invention. This description is not to be taken in a limiting sense, but is merely for the purpose of illustrating the general principles of embodiments of the invention. Furthermore, there is no intention to be bound by any theory presented in the preceding background of the invention or the following detailed description of the invention. The scope of the invention is defined by the appended claims.

Figure 1:
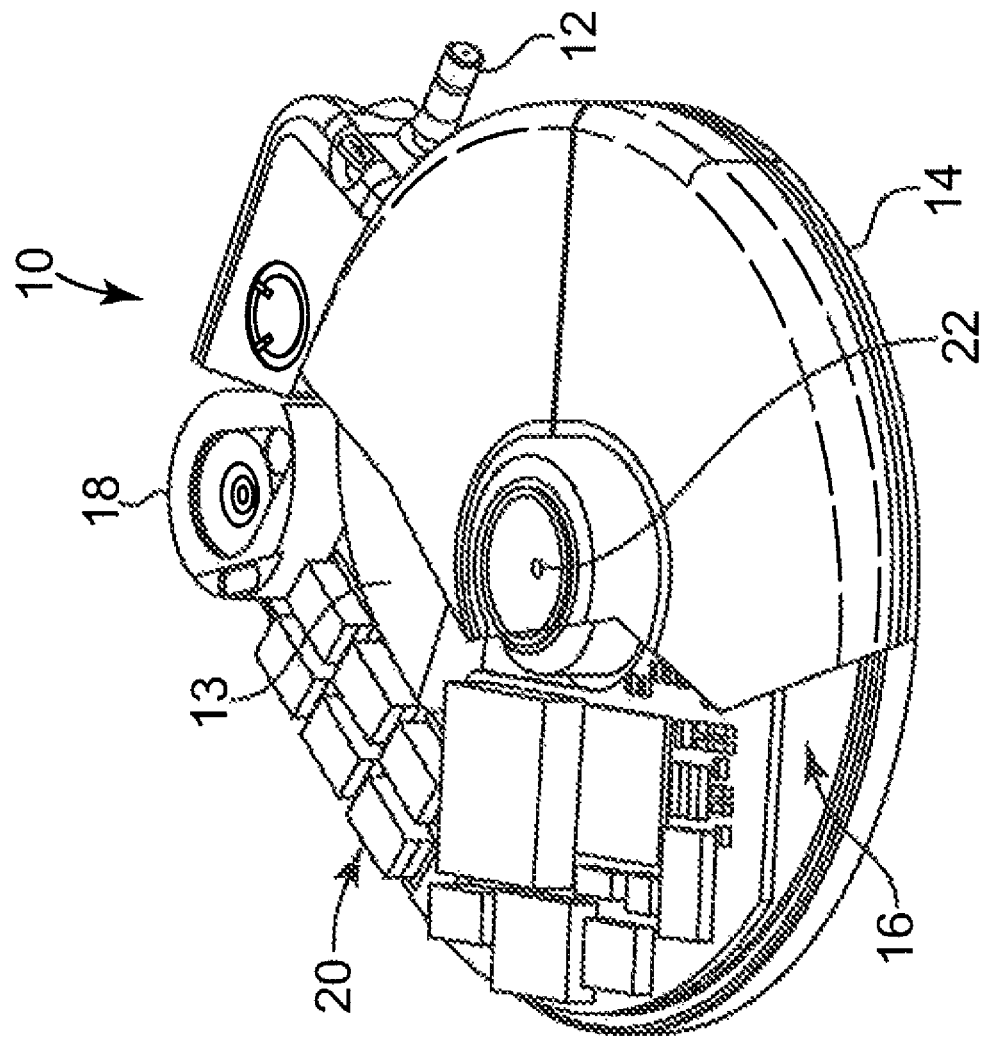
FIG. 1 is an isometric view of an implantable infusion device in accordance with one embodiment of the present invention.

FIG. 1 shows an implantable infusion device 10. The illustrated device 10 is configured to be surgically implanted into a patient, for example, in the abdominal region, between the skin and the abdominal wall. A catheter (not shown) connected to the infusion device 10 may deliver infusion medium to the patient, for example, but not limited to, by feeding infusion medium to a particular location in the venous system, within the spinal column, or in the peritoneal cavity of the patient. Other embodiments of the infusion device 10 may be implemented as external infusion devices that connect to patients through suitable catheter devices or the like. Yet further embodiments of the infusion device 10 may be used in other contexts, e.g., for delivery of a medium into other suitable environments. Therefore, for purposes of simplifying the present disclosure, the term "patient" is used herein to refer to any environment in which an implantable device is implanted or to which an external device is connected, whether or not the implant or connection is carried out for medical purposes. Also, the term "infusion medium" is used herein to refer to any suitable medium delivered by the drive device.

In further embodiments, the present invention actuator member may be included in pumping systems not related to infusion devices.

The device 10 may include a generally disc-shaped housing 14. While a generally circular disc-shaped embodiment is illustrated in FIG. 1, it will be understood that further embodiments of the infusion device 10 may employ housing of other shapes, including, but not limited to, oval, oblong, rectangular, or other curved or polygonal shapes. Generally, the housing 14 is made of a biocompatible material and most often has a relatively small diameter and thickness to reduce patient trauma during implant surgery and after implantation.

The housing 14 includes a reservoir 16 for holding a volume of infusion medium, such as, but not limited to, a liquid medication to be administered to the patient. Housing 14 may also contain a drive mechanism 18 (e.g. a pump), a power source 13, and control electronics 20. Pump 18 may be configured to receive infusion media from reservoir 16 via a pump inlet 22. Inlet structure 22 may provide a closeable and sealable fluid flow path to the reservoir in the reservoir portion of the housing. The inlet structure may include a port for receiving a needle through which fluid may be transferred to the infusion device, for example, to fill or re-fill the reservoir of the device with the infusion media or a rinsing fluid as will be more fully discussed below. In particular embodiments, the inlet structure may be configured to re-seal after a fill or re-fill operation, and to allow multiple re-fill and re-seal operations. One example of an inlet structure is described in U.S. Pat. No. 6,652,510, titled "Infusion Device and Reservoir for Same," which is incorporated by reference herein in its entirety and for everything it teaches and discloses. However, further embodiments may employ other suitable inlet structures, including, but not limited to, those described in U.S. Pat. Nos. 5,514,103 and 5,176,644, each to Srisathapat et al.; U.S. Pat. No. 5,167,633 to Mann et al.; U.S. Pat. No. 4,697,622 to Swift; and U.S. Pat. No. 4,573,994 to Fischell et al., also incorporated by reference. Representative examples of reservoir housing portions and reservoirs which may be employed in embodiments of the invention are described in the above referred to U.S. Pat. No. 6,652,510, and further embodiments may employ other suitable reservoir configurations, including, but not limited to, those described in the above referred to U.S. Pat. Nos. 5,514,103; 5,176,644; 5,167,633; 4,697,622; and 4,573,994.

Figure 2:
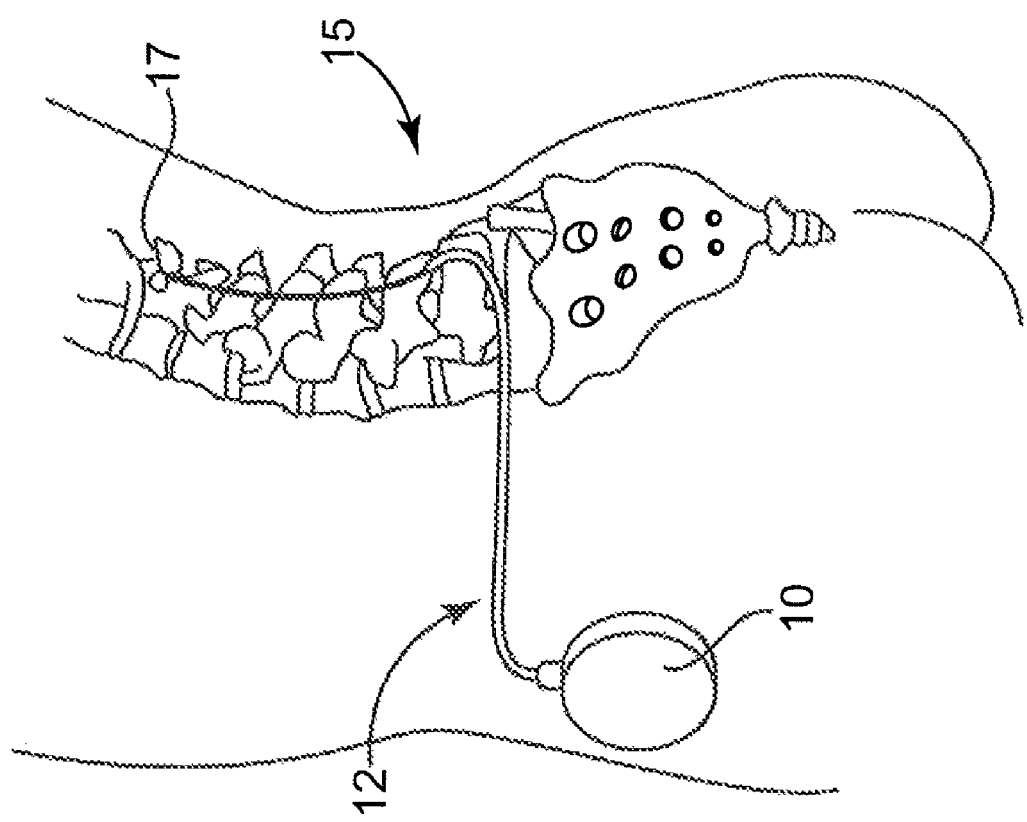
FIG. 2 is a representative view of an infusion device implanted into a body of a patient in accordance with one embodiment of the present invention

FIG. 2 may illustrate an example placement of one embodiment of an implantable infusion system that is implanted within a patient's body 15. The exemplary infusion systems depicted in implantable medical device 10, and preferably at least one catheter 12. Such infusion systems may be used for a wide variety of therapies including treatment of pain, spasticity, and other medical conditions. Although exemplary infusion systems that may be used in connection with the present invention are described herein, reference may also be had to U.S. Patent Application Publication No. US 2005/0075624 A1, titled Pressure Sensing in Implantable Medical Devices (Miesel), which describes infusion systems that may be modified for use accordance with the methods of the present invention.

The medical device 10 and catheter 12 are typically implanted by a clinician (e.g., surgeon) within the body 15 during a surgical procedure. While the present invention also contemplates embodiments wherein the catheter is implanted with a proximal end outside the body 15 so that it may attach to an external infusion device, the remainder of this description is, for the sake of brevity, directed to implantable infusion systems that are entirely implanted in the body 15 of the patient.

Before implantation of the medical device 10, the catheter 12 may be positioned such that the fluid delivered to the patient through the catheter 12 reaches a selected internal delivery location 17 within the body 15 of the patient. As depicted, the infusion system is implanted such that the delivery site 17 is located within the intrathecal space of the spinal canal. As may be appreciated, the infusion systems of the present invention may be used to deliver fluid to any other selected internal delivery location, e.g., epidural, etc.

Catheter 12 may preferably disgorge fluid at other than at its distal end. For example, catheter 12 may intentionally have a delivery region that is not proximate the distal end of the catheter 12, e.g., a hole or valve positioned somewhere before reaching the distal end of the catheter 12. Thus, catheter 12 may be placed in patient with a delivery region of catheter 12 placed in or near to, generally proximate to, the selected internal delivery site 17.

A proximal end of the catheter 12 may be tunneled through the tissue to the device implant location and coupled to a catheter port of the medical device 10. If implanted, the medical device 10 is typically positioned subcutaneously, e.g., from 1 centimeter (0.4 inches) to 2.5 centimeters (1 inch) beneath the skin, where there is sufficient tissue for supporting the medical device 10, e.g., with sutures or the like.

The medical device 10 is, in the illustrated embodiment, operable to infuse a fluid from an enclosed reservoir into the body 15 through the catheter 12.

Figure 3:
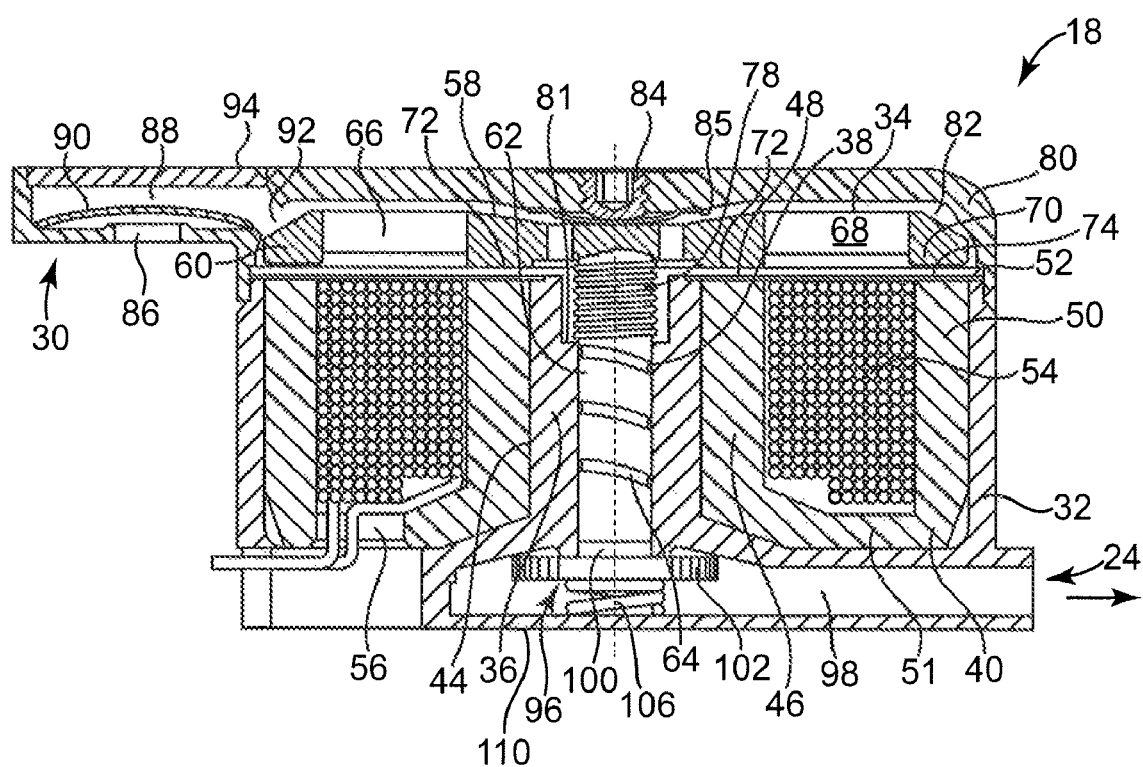
FIG. 3 is a cross-sectional view of a drive mechanism in accordance with a first embodiment of the present invention.

As illustrated in FIG. 3, pump 18 may include an outlet 24 through which the infusion medium may be expelled. When the device 10 is implanted in a patient or connected externally to a patient, the catheter 12 may be connected to the outlet 24 to deliver expelled infusion medium into the patient's blood stream or to a selected location in the patient's body. The drive mechanism may be controlled to deliver infusion medium in any suitable manner, for example, according to a programmed dispensing rate or schedule or according to an actuation signal from a sensor, timer or other suitable source.

In particular embodiments, both the drive mechanism 18 and the reservoir 16 may be hermetically sealed. In such embodiments, the housing 14 containing drive mechanism 18 and control electronics 20 may be made from titanium or titanium alloy or other biocompatible metals. The reservoir portion 16 of the housing may be made from similar metals or a biocompatible and infusion medium compatible plastic that allows for the desired hermeticity.

The drive mechanism 18 may include mechanical and electromagnetic components that inhabit a volume of space within the housing 14 in which the components reside and operate. The device 10 is configured such that, once implanted, it functions for a relatively long period of time to administer infusion medium to the patient to periodically be replenished from the outside of patient's body.

As used herein, the term "therapeutic substance" refers to a substance intended to have a therapeutic effect on the patient, e.g., pharmaceutical compositions, genetic materials, biologics, and other substances. "Pharmaceutical compositions," as used herein, may include chemical formulations intended to have a therapeutic effect such as intrathecal antispasmodics, pain medications, chemotherapeutic agents, and the like. Pharmaceutical compositions are often configured to function effectively in an implanted environment by possessing various characteristics including: stability at body temperature to retain therapeutic qualities; concentration to reduce the frequency of replenishment; and the like. "Genetic materials," as used herein, may include substances intended to have a direct or indirect genetic therapeutic effect such as genetic vectors, genetic regulator elements, genetic structural elements, DNA, and the like. "Biologics," as used herein, may include substances that are living matter, or derived from living matter, and offer a therapeutic effect to the patient such as stem cells, platelets, hormones, biologically produced chemicals, and the like. "Other substances" may include most any other substance that is intended to have a therapeutic effect, yet does not clearly fit within one of the categories identified above. Examples of other substances may include saline solutions, fluoroscopy agents, and the like.

In some embodiments, the fluid contained within a reservoir of the medical device 10 may be replenished periodically after device implantation. Typically, replenishment is accomplished with a non-coring needle (not shown) connected to a syringe filled with the fluid. The needle may be inserted through the patient's skin and into a self-sealing septum located within the housing of the medical device 10.

In order to fully understand the operation of the present invention, a review of an example embodiment pump in which the invention may be utilized may be first helpful.

FIG. 3 is a cross-sectional view of a drive mechanism 18 in a retracted position or state. The pump 18, also known as the drive mechanism 18, may employ electromagnetic and mechanical forces to change (or move) between retracted and forward positions or states, also known as first and second positions or states, to cause infusion medium to be drawn in through the inlet 30 and forced out of the outlet 24, respectively. The assembly of components shown in FIG. 3 is also shown in an exploded view in FIG. 4.

Figure 4:
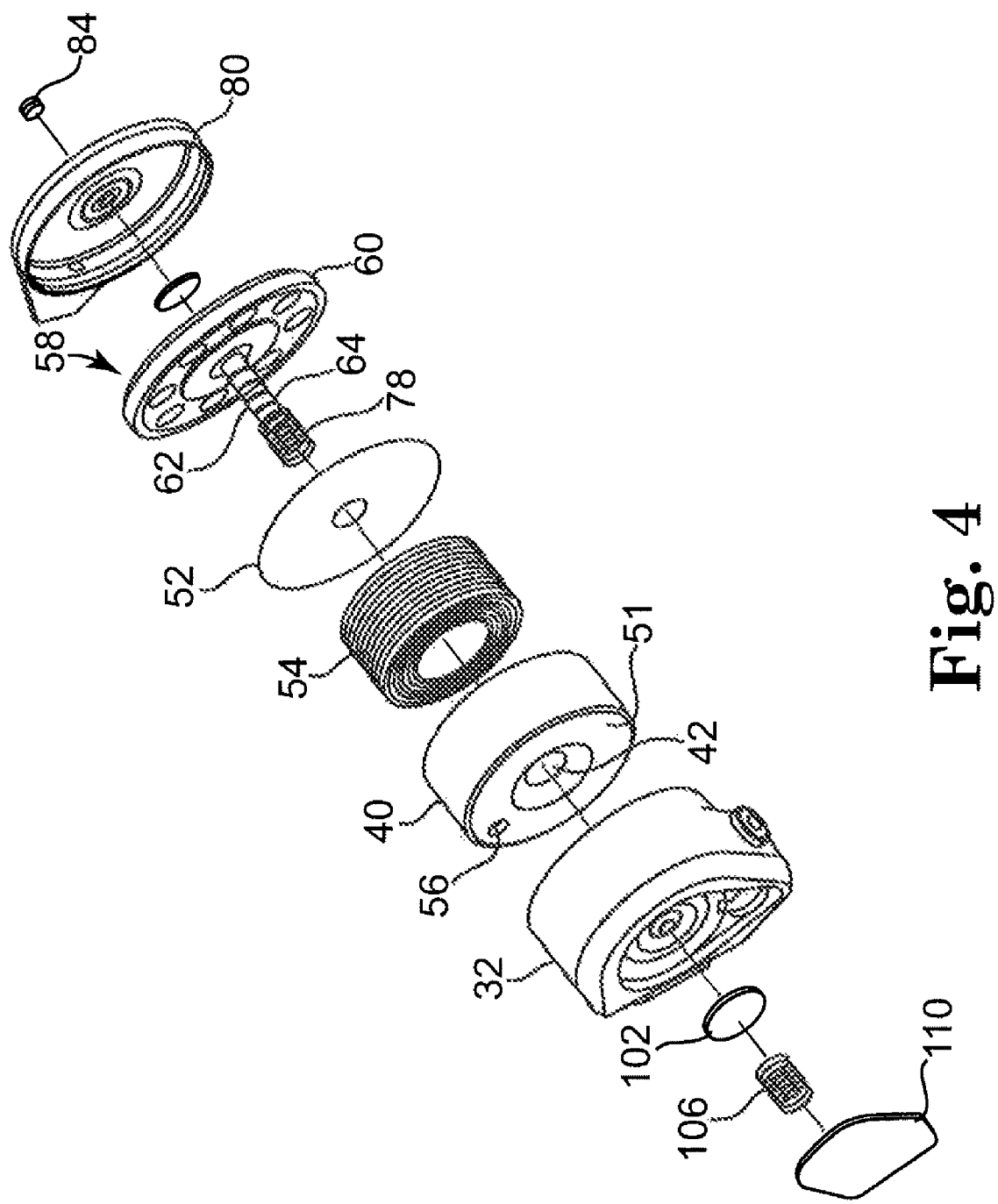
FIG. 4 is an exploded view of an embodiment of the drive mechanism shown in FIG. 3.

Referring to FIGS. 3 and 4, the drive mechanism 18 may include a housing member 32 that is open on one side to a hollow, annular interior section 34. The housing 32 has a central hub portion 36 with a central piston channel 38. The bottom side of the housing member 32 (with reference to the orientation shown in FIG. 3) includes an opening to the hollow interior section 34 through which coil wires may pass. The bottom side of the housing member may also include a configuration of recesses and cavities for providing an outlet chamber and an outlet passage. The housing member 32 is most often made of generally rigid, biocompatible and infusion medium compatible material having no or low magnetic permeability such as, but not limited to, titanium, stainless steel, bio-compatible plastic, ceramic, glass or the like.

As shown in FIGS. 3 and 4, a coil cup 40 is located within the annular interior section 34 of the housing 32. The coil cup 40 may have a generally cylinder shape, open on one side to a hollow, annular interior. The coil cup 40 may include a bore 42 located in a central hub portion 44 and extending axially relative to the annular interior. The hub portion 44 of the cup member defines an inner annular wall 46 having an end surface 48 (or inner pole surface) having a defined width. The cup member 40 has an outer wall 50 having an end surface 52 (or outer pole surface) having a width. The outer wall 50 is connected to the inner wall 46 of hub portion 44 by a backiron portion 51 of the cup member 40. At the open end of cup member 40 the end surfaces 48 and 52 of the inner and outer walls 46 and 50, respectively, define pole surfaces that cooperate with pole surfaces on an armature to provide a path for electromagnetic flux during a forward stroke of the drive mechanism.

When assembled, the coil cup 40 may be located in the hollow interior of the housing member 32, with the central portion 36 of the housing 32 extending through channel 42 of the coil cup 40 as shown in FIG. 3. A coil 54 may be located within the hollow, annular interior of the coil cup 40 and disposed around the axis of the annular interior of the coil cup 40. The coil cup 40 is provided with an opening 56 through which coil leads extend, as shown in FIGS. 3 and 4. The coil cup 40 may be made of generally rigid material having a relatively high magnetic permeability such as, but not limited to, low carbon steel, iron, nickel, ferritic stainless steel, ferrite, other ferrous materials, or the like. The coil 54 may include a conductive wire wound in a coil configuration. The coil wire may include any suitable conductive material such as, but not limited to, silver, copper, gold or the like, with each turn electrically insulated from adjacent turns and the housing. In one particular embodiment, the coil wire may have a square or rectangular cross-section to achieve minimal space between windings and a greater number of coil turns thus improving electrical efficiency.

The drive mechanism 18 may also includes an actuator member 58, which may include an armature portion 60 and a piston portion 62. The actuator member 58 is most often made of a generally rigid, biocompatible and infusion medium compatible material having a relatively high magnetic permeability such as, but not limited to, ferrous materials, ferritic stainless steel with high corrosion resistance, or the like. In the embodiment of FIGS. 3 and 4, the actuator (with an armature portion 60 and a piston portion 62) may be formed as a single, unitary structure.

Figure 5:
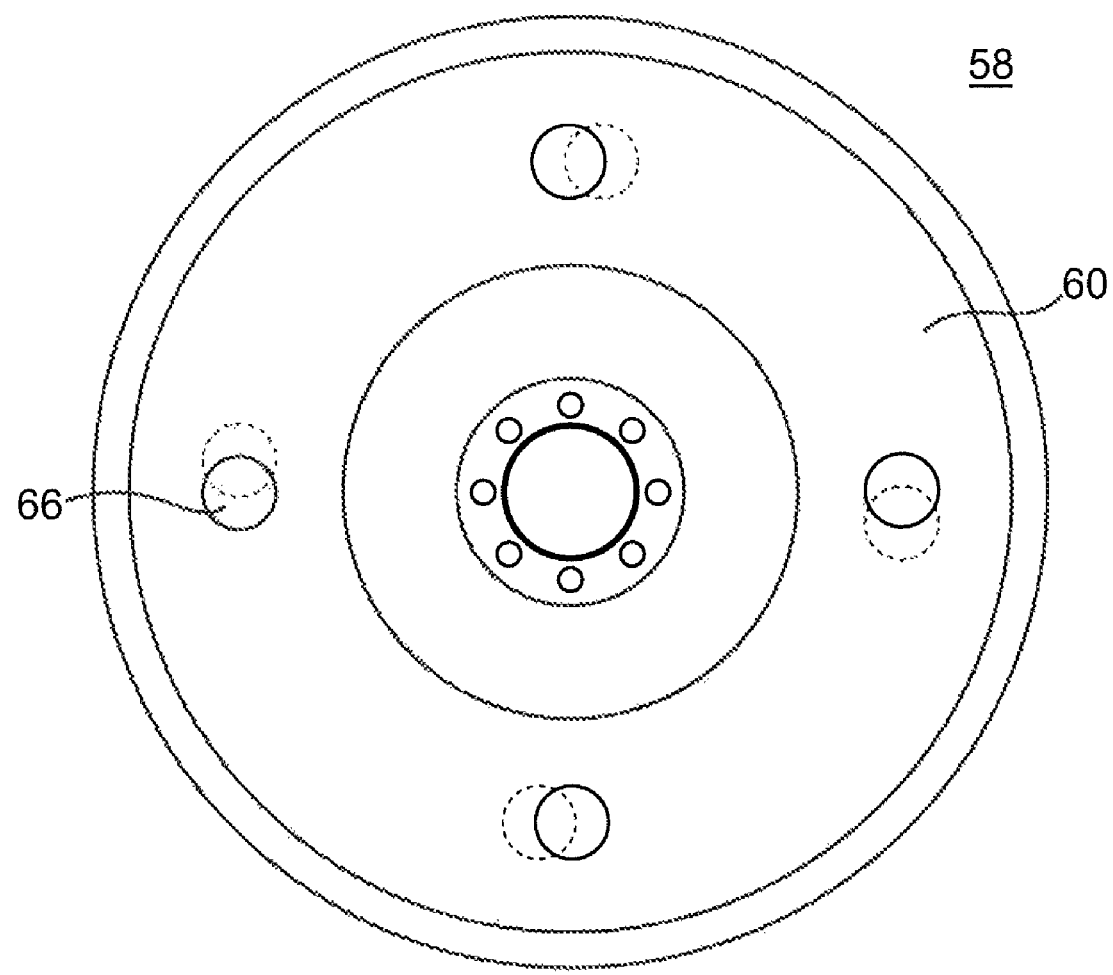
FIG. 5 is a top elevation view of one embodiment of an actuator member of the present invention.

A perspective view of one embodiment actuator member 58 of the present invention is shown in FIG. 5, where the armature portion 60 of the actuator member has a round, disc shape, and may be provided with at least one opening 66. In other embodiments, a plurality of openings 66 may be provided. The opening 66 in the illustrated example is set at a pre-determined angle through the armature portion 60 of the actuator member 58. The openings 66 may be referred to by other names, including, but not limited to, channels, cut outs, fissures, slits, contours, etc. The angle of the opening 66 through the armature 60 is selected such that the passage of the fluid through the opening 66 as the actuator member 58 is drawn down by the coil causes the actuator member 58 to rotate about a generally longitudinal axis of the piston 62 and generally perpendicularly through the center of the armature 60. The opening 66 may be aligned along the angle of rotation desired. The rotation of the actuator member 58 is further described below.

The armature 60 cooperates with the inner and outer walls of the coil cup 40 to provide a flux path for electromagnetic flux. The spacing between the pole surfaces on the armature 60 and the pole surfaces on the coil cup walls define gaps in the flux path. In particular embodiments, the spacing between the surface of outer pole 70 of the armature 60 and the surface of outer pole 52 of the outer wall 50 of the coil cup 40 is greater than the spacing between the surface of inner pole 72 of the armature and the pole surface 48 of the inner wall 46 of the coil cup (or the barrier 74) when the actuator is in the retracted position shown in FIG. 3.

The radial struts 68 in the armature provide radial paths for electromagnetic flux between the outer and inner pole sections 70 and 72 of the armature. The configuration of openings is most often designed to provide a sufficient conductor for electromagnetic flux and yet minimize or reduce viscous resistance to actuator motion. With reference to FIG. 3, the actuator member 58 is arranged with the piston portion 62 extending through the axial channel 38 of the housing 32 and with the armature portion 60 positioned adjacent to the open side of the coil cup 40. An actuator spring 78 may be positioned to force the armature portion 60 of the actuator 58 in the direction away from the open side of the coil cup 40 to provide a gap between the armature 60 and the open side of the coil cup 40. A biocompatible and infusion medium compatible barrier 74 is located over the open side of the coil cup 40 between the armature 60 and the coil cup 40 to help seal the annular interior of the coil cup 40 and coil 54. In other embodiments in which infusion medium may contact the coil, the barrier 74 may be omitted.

The actuator spring 78 in the illustrated embodiment is a coil spring disposed around the piston portion 62 of the actuator 58 adjacent the armature portion 60. One end of the coil spring abuts the armature portion 60 of the actuator, while the opposite end of the coil spring abuts a shoulder 81 in the piston channel 38 of the housing 32. In this manner, the actuator spring 78 imparts a spring force between the housing and the actuator 58 to urge the actuator toward its retracted position shown in FIG. 3.

In the illustrated embodiment, by using a coil spring 78 located around and coaxial with the piston portion 62 and disposed partially within the piston channel 38, the actuator spring may have minimal or no contribution to the overall thickness dimension of the drive mechanism. However, in other embodiments, actuator springs may have other suitable forms and may be located in other positions suitable for urging the actuator toward its retracted position shown in FIG. 3. The actuator spring 78 is most often made of a biocompatible and infusion medium compatible material that exhibits a suitable spring force such as, but not limited to, titanium, stainless steel, MP35N cobalt steel or the like.

The drive mechanism 18 may further include a cover member 80 which attaches to the housing member 32 over the open side of the housing member and the barrier 74. The cover member 80 is most often made of a generally rigid, biocompatible and infusion medium compatible material having a relatively low magnetic permeability (being relatively magnetically opaque) such as, but not limited to, titanium, stainless steel, biocompatible plastic, ceramic, glass or the like.

The cover member 80 defines an interior volume 82 between the barrier 74 and the inner surface of the cover member. The armature portion 60 of the actuator member 58 resides within the interior volume 82 when the cover is attached to the housing. The armature 60 is moveable in the axial direction within the volume 82 between the retracted position shown in FIG. 3 and the forward stroke position, which is described in more detail below. This movement is created by the action of electromagnetic force generated when a current is passed through the coil 54 and the mechanical return action of the actuator spring 78.

An adjusting plunger 84 may be located within the cover 80 for contacting the armature 60 when the armature is in the fully retracted position shown in FIG. 3 to set the retracted position of the armature. In particular embodiments, a seal (e.g. a silicon rubber sealing ring) may be disposed between the plunger 84 and the cover member 80. In further embodiments, a flexible diaphragm 85 (such as, but not limited to, a thin titanium sheet or foil) may be coupled to the inside surface of the cover 80 and sealed around the opening through which the plunger 84 extends. The diaphragm will flex to allow the plunger to define an adjustable retracted position whiles also providing sealing functions for inhibiting leakage at the interface between the plunger 84 and the cover 80. In other embodiments, after a proper armature position is set, the plunger is fixed in place with respect to the cover member, for example, by adhering the plunger to the cover member with one or more welds, adhesives or other securing methods.

The cover member 80 may include the inlet 30 of the drive mechanism, which has an inlet opening 86 in fluid flow communication with the interior volume 82. The inlet opening 86 connects in fluid flow communication with the reservoir of the infusion device 10 (FIG. 1) to receive infusion medium from the reservoir.

The inlet opening 86 provides a flow path to an inlet chamber 88 formed in the cover member 80 adjacent the inlet opening. A filter or screen member, such as a porous or screen material 90, may be disposed within the inlet chamber 88. The filter or screen member 90 is provided in a flow path between the inlet opening 86 and an inlet port 92 to the volume 82. A one-way inlet valve (not shown) may also be provided in the flow path between the inlet opening 86 and the inlet port 92 or within the inlet port 92 to allow medium to flow into but not out of the interior volume 82 through the inlet. The cover member 82 may be provided with an inlet cover 94 that, when removed, allows access to the inlet chamber 88 to, for example, install, replace or service a filter 90 or inlet valve, or to service or clean the inlet 86.

As shown in FIG. 3, the piston portion 62 of the actuator 58 may extend through the axial channel 38 in the housing 32 toward an outlet chamber 98 at the end of the axial channel 38. The channel 38 may have an inside diameter which is larger than the outside diameter of the piston portion 62. As a result, an annular volume is defined between the piston portion 62 and the wall of the axial channel 38 along the length of the axial channel 38. Infusion medium may flow through the annular volume 82 within the cover 80 to a piston chamber 100 located between the free end of the piston portion 62 and a valve member 102 of a valve assembly 96. In particular embodiments, the radial spacing between the piston portion 62 and the wall of the channel 38 is selected to provide a suitable flow toward the piston chamber 100 to refill the piston chamber 100 (during a return stroke of the piston portion), but small enough to sufficiently inhibit back flow of medium from the piston chamber 100 (during a forward stroke of the piston portion).

The actual radial spacing between the piston portion 62 and the wall of the channel 38 to achieve such results depends, in part, on the overall dimensions of those components, the pressure differentials created in the mechanism, and the viscosity of the infusion medium.

The valve assembly 96 in the embodiment of FIG. 3 may further include the valve member 102 and a valve spring 106. The valve member 102 is located within the outlet chamber 98 and, as shown in FIG. 3, is positioned to close the opening between the axial channel 38 and the outlet chamber 98 when the actuator 58 is in the retracted position. During the forward stroke, the valve member 102 is positioned to open a flow passage between the axial channel 38 and the outlet chamber 98. The valve spring 106 is located within the outlet chamber 98 to support the valve member 102. The spring 106 imparts a spring force on the valve member 102 in the direction toward piston 62 urging the valve member 102 toward a closed position to block the opening between the axial channel 38 and the outlet chamber 98.

The valve member 102 is most often made of generally rigid, biocompatible and infusion medium compatible material, such as, but not limited to, titanium, stainless steel, biocompatible plastic, ceramic, glass, gold, platinum or the like. A layer of silicon rubber or other suitable material may be attached to the rigid valve member material on the surface facing the channel 38 to help seal the opening to channel 38 when the valve member is in the closed position shown in FIG. 3.

The valve spring 106 is most often made of biocompatible and infusion medium compatible material that exhibits a suitable spring force such as, but not limited to, titanium, stainless steel, MP35N cobalt steel or the like. In the illustrated embodiment, the valve spring 106 is a coil spring. In other embodiments, other suitable valve spring configurations may be employed, including, but not limited to, helical, flat, radial, spiral, barrel, hourglass, constant or variable pitch springs or the like.

The embodiment shown in FIG. 3 utilizes a valve cover 110 sealed to the housing 32 to enclose the outlet chamber 98. The valve cover 110 is most often made of a generally rigid, biocompatible and infusion medium compatible material, such as, but not limited to, titanium, stainless steel, biocompatible plastic, ceramic, glass, gold, platinum or the like.

The coil 54 may be inserted into the annular interior of the coil cup 40 with the coil leads extended through a coil lead opening 56 in the coil cup. The coil may be impregnated or partially impregnated with a fill material of epoxy or the like for adhering the coil to the coil cup and for sealing or partially sealing the coil. The fill material may also be used to adhere the barrier plate to the coil members to avoid warping or bulging of the barrier plate after assembly.

The coil cup 40 and the coil 54 may be inserted into the interior of the housing 32 with the coil leads (which may be wire leads or flexible conductive tabs) extending through a coil lead opening 56 in the housing 32. In particular embodiments, the coil cup and housing are configured to provide a tight friction fit that does not require additional means to adhere the two components together. In other embodiments, the coil cup 40 and housing 32 may be coupled together by a suitable adhesive material or other adhering methods, including, but not limited to, welding, brazing or the like.

The barrier 74 may be placed over the coil, coil cup and housing sub-assembly. The barrier 74 may be adhered to the housing by one or more adhering points or continuously secured along the circumference of the barrier 74 with any suitable adhesive material or other adhering methods including, but not limited to, welding, brazing, soldering, or the like. Alternatively, or in addition, the barrier 74 may be held in place by a shoulder portion of the cover 80, as shown in FIG. 3. In addition, as noted above, the barrier 74 may be adhered to the coil 54 by fill material in the coil. In particular embodiments, the barrier 74 is held in a generally flat position relative to the coil cup and coil. To enhance this flat relationship, the coil cup and housing may be assembled together and then machined to planarize the barrier contact surfaces prior to inserting the coil in the coil cup and prior to adding fill material to the coil.

After the barrier 74 is placed over the coil, coil cup and housing, the actuator 58 may be added to the sub-assembly. First, however, the actuator spring 78 is placed around the piston portion 62 adjacent the armature portion 60 of the actuator. Then the free end of the piston portion 62 is passed through the axial channel 38 of the housing 32 with the armature end of the actuator arranged adjacent the barrier 74.

The volume of piston chamber 100, the compression of the actuator spring 78, and the position of the actuator 58 in the retracted position shown in FIG. 3 may be adjusted by adjusting the position of the adjusting plunger 84. In one particular embodiment, the adjusting plunger 84 includes a threaded cylindrical member that engages corresponding threads in a plunger aperture in the cover member 80 to allow adjustment in a screw-threading manner. The diaphragm 85 under the plunger 84 contacts the armature portion 60 of the actuator inside of the cover member 80. The other end of the plunger 84 may be provided with a tool-engagement depression for allowing engagement by a tool, such as a screw-driver, Allen wrench or the like, from outside of the cover member 80. By engaging and rotating the plunger 84 with a suitable tool, the depth that the plunger extends into the cover member 80 may be adjusted to adjust the retracted position of the armature portion 60 relative to the barrier 74 (to adjust the gaps between the pole sections 70 and 72 of the armature and pole sections formed by the coil cup 40 when the actuator is in the retracted position of FIG. 3). In one particular embodiment, adjustments of the plunger 84 are made during manufacture. In that embodiment, the adjusted position is determined and set by welding or otherwise adhering the plunger 84 in the adjusted position during the manufacture. In other embodiments, the plunger 84 is not set and welded during manufacture to allow adjustment of plunger 84 after manufacture.

Figure 6:
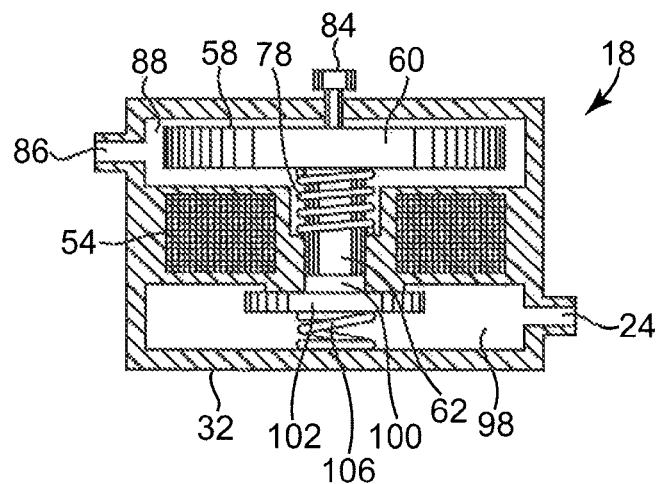
FIGS. 6, 7, and 8 are simplified cross-sectional views of the drive mechanism shown in FIG. 3 in quiescent, forward, and retracted states, respectively.
Figure 7:
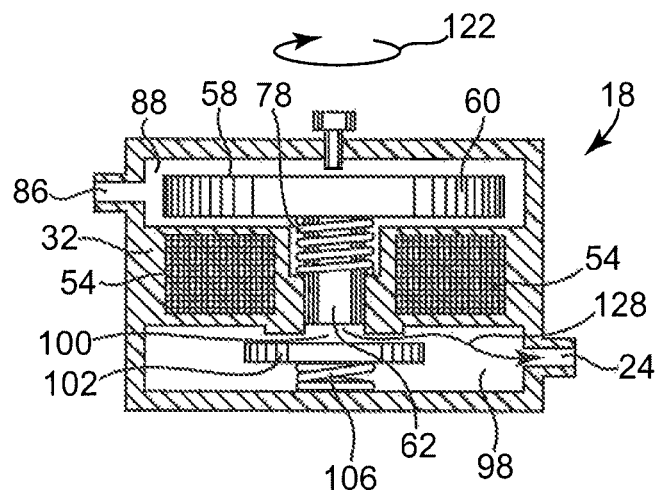
Figure 8:
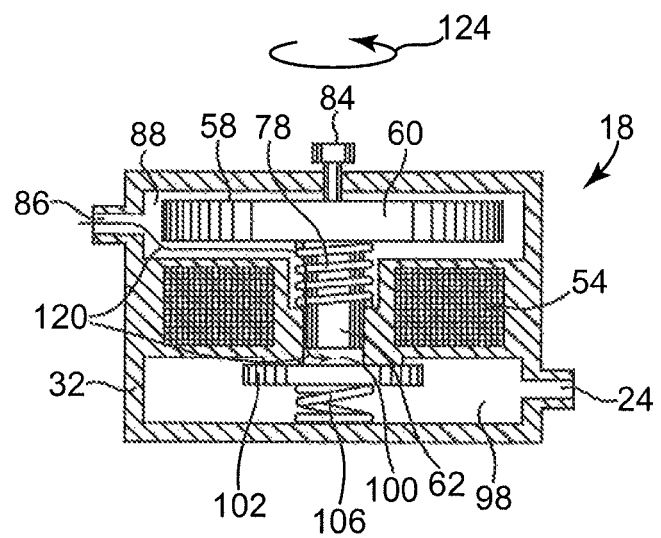
Figure 9:
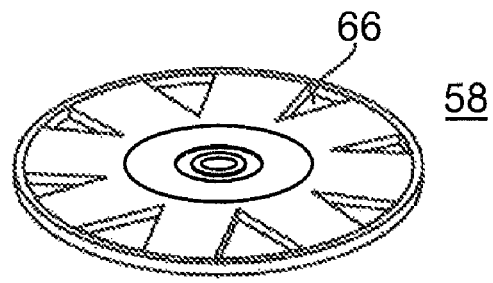
FIGS. 9, 10, 11, and 12 are perspective views of various embodiments of the armature portions of the actuator member of the present invention.
Figure 10:
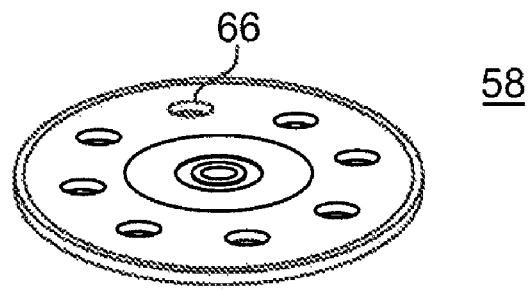
Figure 11:
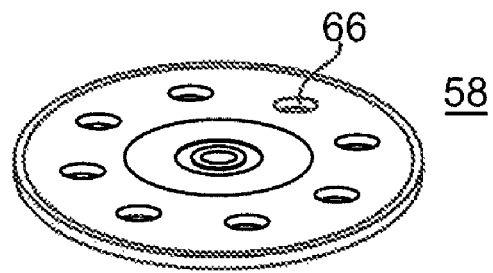
Figure 12:
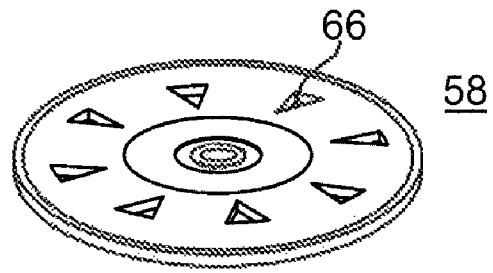

FIGS. 6, 7 and 8 are simplified cross-sectional views of the drive mechanism 18 shown in FIG. 3 and will be useful in explaining the operation of drive mechanism 18 and the rotational movement of the actuator member 58. In the interest of clarity, only major functional features and components are illustrated, and these are identified by reference numerals corresponding to reference numerals used in FIG. 3 to denote like features and components.

A simplified description the pump stroke of pump 10 may be helpful to further describe the movement of actuator 58.

FIG. 6 illustrates drive mechanism 18 in its first (retracted) quiescent state. Drive mechanism 18 employs electromagnetic and mechanical forces to move between a retracted, or first, position (FIG. 6) and a forward, or second, (FIG. 7) position to cause infusion medium to be drawn into and driven out of the drive mechanism 18 in a controlled manner. In FIG. 6 valve member 102 is fully extended under the force of spring 106, piston chamber 100 and inlet chamber 88 are substantially filled with infusion media (or rinsing media as the case may be), and coil 54 is de-activated, i.e., not energized or inadequately energized, such that the force exerted by the coil 54 on the actuator member 58 is not enough to overcome the force of spring 78. In the retracted position, the spring 78 urges the actuator 58 toward its retracted position shown in FIG. 6. When the coil 54 is energized sufficiently to overcome the spring force of spring 78, the actuator 58 moves through the fluid to the forward stroke position shown in FIG. 7. The movement of the actuator between retracted and forward positions creates pressure differentials within the internal chambers and volumes of the drive mechanism 18 to draw medium into the inlet 86 and drive medium out the outlet 24. More specifically, when the coil 54 is de-activated, the actuator 58 is held in its retracted position (FIGS. 6 and 8) under the force of the spring 78. When coil is de-activated immediately following a forward stroke, the spring 78 moves the actuator 58 to the retracted position of FIG. 8 from the forward position shown in FIG. 7, and then ultimately back to the position shown in FIG. 6.

As the actuator 58 retracts, the piston portion 62 of the actuator is retracted relative to the valve member 102 such that a piston chamber 100 volume is formed between the end of the piston portion 62 and the valve member 102. The formation of the piston chamber 100 volume creates a negative pressure which draws infusion medium (or rinsing fluid) from the inlet chamber 88 and into the piston chamber 100 as is indicated by arrows 120. While not shown, one or more channels could be provided through the piston portion 62 to provide one or more additional flow paths to the piston chamber 100 if desired.

As the armature portion 60 of the actuator is drawn toward the coil cup 40, the piston portion 62 of the actuator is moved axially through the channel 38 in the direction toward the outlet chamber 98. With the coil energized, the piston portion 62 continues to move under the action of the armature 60 until a mechanical stop is reached, for example, mechanical contact of the actuator 58 with the barrier 74, a portion of the housing 32 or cover member 80 (see FIG. 3). In other embodiments, the motion may continue until the return force of the spring and fluid pressure overcomes the electromagnetic force provided by energizing the coil.

When the coil is deactivated and the piston portion 62 is moved back to its retracted position, the pressure in the piston chamber 100 reduces and the valve member 102 is reseated under the action of the valve spring 106. This prevents fluid from flowing back into the drive mechanism through the outlet. In addition, a negative pressure is created in the piston chamber 100 to draw medium into the chamber for the next forward stroke.

In this manner, energization of the coil 54 to move the actuator 58 to its forward position (FIG. 7) may cause a measured volume of medium to be discharged from the outlet. When the coil 54 is de-energized, the actuator 58 is returned to the retracted position under the force of spring 106 and an additional volume of medium is drawn into the piston chamber 100 for the next discharging operation.

As the actuator member 58 moves through the fluid during the pumping stroke, the angled openings 66 through the armature portion 60 cause the actuator member 58 to rotate a predetermined amount. The rotation may be in either direction as desired, but the rotation of the present embodiment is shown by arrow 122 as clockwise. As may be appreciated, the amount of rotation of the actuator member 58 may depend on the viscosity of the fluid, the amount of material being pumped, stroke length, the angle of the opening through the armature 60, the shape and number of the openings 66, and other factors. After the pumping stroke of the actuator member 58, a return stroke is caused by the spring 106. The return stroke may cause the actuator member 58 to rotate some amount in the opposite direction counter to the rotation caused by the pumping stroke (arrow 122), due to the fluid flowing through the opening 66 in the opposite direction. However, the movement of the actuator member 58 in responses to the energized coil 54 during the pumping stroke is relatively quick as compared to the return stroke speed of the actuator member 58 as powered by the coil 54. The rotational movement of the actuator member 58 during the pumping stroke therefore may be a greater amount than the rotational distance of the actuator member 58 during the return stroke, resulting in a net rotation gain in the direction favored by the pumping stroke. As previously mentioned a number of factors may influence the net amount of rotation achieved by each pumping and return stroke. In addition, the opening 66 should be designed in such a manner so as to not cause actuator 58 to tilt off axis during the rotational movement.

The net rotation achieved by each pumping and return stroke may be selected to not be divisible into a perfect 360° circle. As such, a wear pattern will not develop in the components of the pump 10 such as the actuator member 58 and the piston channel 38. Alternatively, the degradation or wear may still develop in a pattern but may develop at a reduced rate due the wear not accruing in the same location during each successive stroke.

FIGS. 9-12 illustrate a number of alternative embodiment shapes for opening 66 in actuator member 58. As may be appreciated, the shape, size, and angle of the opening 66 may be varied by those of skill in the art. Furthermore, the opening 66 may take on different shapes, sizes, and angles in the same actuator member 58. In further embodiments the armature 60 may resemble a fan blade or propeller, including a number of different arms that are or are not attached along an edge. In still further embodiments, shapes may be made in the armature 60 and/or piston 62 that cause the actuator 58 to rotate without actually making openings through the armature 60. Such shapes may be made up of grooves or other shapes in the bottom surface of the armature 60 or along the outer edge of the armature.

While at least one exemplary embodiment has been presented in the foregoing detailed description of the invention, it should be appreciated that a vast number of variations exist. It should also be appreciated that the exemplary embodiment or exemplary embodiments are only examples and are not intended to limit the scope, applicability, or configuration of the invention in any way. Rather, the foregoing detailed description will provide those skilled in the art with a convenient road map for implementing exemplary embodiments of the invention, it being understood that various changes may be made in the function and arrangement of elements described in an exemplary embodiment without departing from the scope of the invention as set forth in the appended claims and their legal equivalents.

What is claimed is:

1. An actuator member for a fluid pumping device comprising:
   an armature portion;
   a piston portion operably connected to the armature portion; and
   one or more angled openings formed through the armature portion, wherein in response to a fluid flowing through the angled openings the actuator member rotates about an axis represented by the piston whereby the actuator member rotates in a first direction during a forward pump stroke and rotates in a second opposite direction during a return stroke.

2. The apparatus of claim 1 wherein the openings are generally circular.

3. The apparatus of claim 1 wherein the openings are ovoid.

4. The apparatus of claim 1 wherein armature portion further comprises a number of different blades.

5. The apparatus of claim 1 wherein actuator is made of a material with a high magnetic permeability.

6. The apparatus of claim 1 wherein the actuator is generally rigid.

7. The apparatus of claim 1 wherein the actuator is formed of one or more of ferrous materials or ferritic stainless steel.

8. The apparatus of claim 1 whereby during each forward and return pump stroke the actuator member rotates a first rotational distance in the first direction during the forward pump stroke and rotates a lesser second rotational distance in the second direction during the return stroke.

9. An actuator for delivering fluid through a piston channel from an inlet to an outlet, the actuator comprising:
- an armature having one or more angled openings configured to move between a first position and a second position, the armature including one or more contours formed in the armature; and
- a piston coupled to the armature and moveable within the piston channel,
- whereby movement of the armature and piston from the first position to the second position causes the fluid to flow through the one or more angled openings to cause the actuator to rotate around a longitudinal axis of the piston and whereby the actuator member rotates in a first direction during a forward pump stroke and rotates in a second opposite direction during a return stroke.

10. The apparatus of claim 9 wherein the contours are formed in a bottom surface of the armature.

11. The apparatus of claim 9 wherein armature portion further comprises a number of different blades.

12. The apparatus of claim 9 wherein actuator is made of a material with a high magnetic permeability.

13. The apparatus of claim 9 wherein the actuator is generally rigid.

14. The apparatus of claim 9 wherein the actuator is formed of one or more of ferrous materials or ferritic stainless steel.

15. An apparatus for delivering a fluid, the apparatus comprising:
- a housing;
- an inlet in the housing for receiving the fluid;
- an outlet in the housing for discharging the fluid;
- a piston channel within the housing through which the fluid flows from the inlet to the outlet; and
- an actuator positioned within the housing and moveable between a first position and a second position, the actuator defining a piston chamber for storing fluid received through the inlet when the actuator is in a retracted position, the actuator driving the fluid stored in the piston chamber toward the outlet when the actuator transitions from the retracted position to a forward position, the actuator comprising:
  - an armature including one or more openings therethrough; and
  - a piston coupled to the armature and moveable within the piston channel,
- whereby the actuator rotates around an axis responsive to the fluid flowing through the openings of the armature, the actuator member rotating in a first direction during a forward pump stroke and a rotating in a second opposite direction during a return stroke.

16. The apparatus of claim 15 whereby during each forward and return pump stroke the actuator member rotates a first rotational distance in the first direction during the forward pump stroke and rotates a lesser second rotational distance in the second direction during the return stroke.

17. The apparatus of claim 15 wherein the openings are formed through the armature on a pre-selected path to effectuate the rotation of the actuator when fluid passes therethrough.

18. The apparatus of claim 15 wherein the openings are generally circular in shape.

19. The apparatus of claim 15 wherein the openings through the armature are more than one shape.

20. The apparatus of claim 15 wherein the axis is longitudinally through the piston.

* * * * *